United States Patent
Pohlmann et al.

(10) Patent No.: US 9,687,554 B2
(45) Date of Patent: Jun. 27, 2017

(54) FINASTERIDE AND MINOXIDIL POLYMERIC NANOPARTICLE ITS PROCESS OF PREPARATION, AQUEOUS SUSPENSION CONTAINING THE SAME, PHARMACEUTICAL COMPOSITION, AND ITS USE

(71) Applicants: Biolab Sanus Farmaceutica Ltda., Taboao da Serra (BR); Universidade Federal Do Rio Grande Do Sul-UFRGS, Porto Alegre (BR)

(72) Inventors: Adriana Raffin Pohlmann, Porto Alegre (BR); Denise Soledade Jornada, Porto Alegre (BR); Ludmila Pinheiro Do Nascimento, Porto Alegre (BR); Silvia Staniscuaski Guterres, Porto Alegre (BR)

(73) Assignees: BIOLAB SANUS FARMACEUTICA LTDA., Taboao da Serra (BR); UNIVERSIDADE FEDERAL DO RIO GRANDE DO SUL—UFRGS, Porto Alegre (BR)

( * ) Notice: Subject to any disclaimer, the term of this patent is extended or adjusted under 35 U.S.C. 154(b) by 186 days.

(21) Appl. No.: 14/424,695

(22) PCT Filed: Aug. 30, 2013

(86) PCT No.: PCT/BR2013/000335
§ 371 (c)(1),
(2) Date: Feb. 27, 2015

(87) PCT Pub. No.: WO2014/032152
PCT Pub. Date: Mar. 6, 2014

(65) Prior Publication Data
US 2015/0216986 A1    Aug. 6, 2015

(30) Foreign Application Priority Data
Aug. 31, 2012    (BR) .................... BR102012022036-9

(51) Int. Cl.
*A61K 47/34*    (2017.01)
*A61K 9/51*    (2006.01)
(Continued)

(52) U.S. Cl.
CPC ............ *A61K 47/34* (2013.01); *A61K 9/0014* (2013.01); *A61K 9/06* (2013.01); *A61K 9/08* (2013.01);
(Continued)

(58) Field of Classification Search
CPC .. A61K 2300/00; A61K 31/506; A61K 31/58; A61K 31/473; A61K 47/14;
(Continued)

(56) References Cited

U.S. PATENT DOCUMENTS

| 2006/0204588 A1 | 9/2006 | Liversidge et al. |
| 2011/0117045 A1 | 5/2011 | Aimi et al. |
| 2011/0212167 A1 | 9/2011 | Ali et al. |

FOREIGN PATENT DOCUMENTS

WO    2005000258 A1    1/2005

OTHER PUBLICATIONS

Drake et al., "The effects of finasteride on scalp skin and serum androgen levels in men with androgenetic alopecia." Journal of the American Academy of Dermatology, 1999, vol. 41, No. 4, p. 550-554.
(Continued)

*Primary Examiner* — Aradhana Sasan
(74) *Attorney, Agent, or Firm* — Reed Smith LLP; Mark T. Vogelbacker

(57) ABSTRACT

The present invention relates to a pharmaceutical composition for topical application for the treatment of alopecia, said
(Continued)

composition comprising polymeric nanoparticles, preferably nanocapsules containing two active ingredients, finasteride and minoxidil, additives and a pharmaceutically acceptable carrier. The invention further includes a process for the preparation of polymeric nanoparticles, preferably nanocapsules of finasteride and minoxidil, a composition suitable for topical application for the treatment of alopecia, as well as the use of said nanocapsules for the preparation of a pharmaceutical composition.

16 Claims, 4 Drawing Sheets

(51) Int. Cl.
*A61K 31/473* (2006.01)
*A61K 9/08* (2006.01)
*A61K 9/06* (2006.01)
*A61K 31/506* (2006.01)
*A61K 47/14* (2017.01)
*A61K 9/00* (2006.01)
*A61K 9/58* (2006.01)
*B82Y 5/00* (2011.01)
*A61K 31/58* (2006.01)

(52) U.S. Cl.
CPC .............. *A61K 9/51* (2013.01); *A61K 9/5123* (2013.01); *A61K 31/473* (2013.01); *A61K 31/506* (2013.01); *A61K 31/58* (2013.01); *A61K 47/14* (2013.01); *B82Y 5/00* (2013.01)

(58) Field of Classification Search
CPC ........ A61K 47/34; A61K 9/0014; A61K 9/06; A61K 9/08; A61K 9/51; A61K 9/5123; B82Y 5/00
See application file for complete search history.

(56) References Cited

OTHER PUBLICATIONS

Inui et al., "Molecular basis of androgenetic alopecia: From androgen to paracrine mediators through dermal papilla." Journal of Dermatological Science, 2011, vol. 61, p. 1-6.

Trueb, "Molecular mechanisms of androgenetic alopecia." Experimental Gerontology, 2002 v. 37, No. 8-9, p. 981-990.

Liu et al. "Different patterns of 5α-reductase expression, cellular distribution, and testosterone metabolism in human follicular dermal papilla cells." Biochemical and Biophysical Research Communications, 2008, 368 p. 858-864.

Ellis, "The genetics of androgenetic alopecia." Clinics in Dermatology, 2001, vol. 19, p. 149-154.

Sinclair, "Male androgenetic alopecia." The Journal of Men's Health & Gender, 2004 v. 1, No. 4, p. 319-327.

Kumari et al., "Biodegradable polymeric nanoparticle based drug delivery systems, Colloids and Surfaces B: Biointerfaces," vol. 75, Issue 1, Jan. 1, 2010, pp. 1-18.

Torchilin et al., "Recent Advances With Liposomes as Pharmaceutical Carriers", Nature Reviews, vol. 4, Feb. 2005, p. 145-160.

Schaffazick et al., "Characterization and physicochemical stability of nanoparticle polymeric systems for drug delivery." New Chemistry, 2003, vol. 26, No. 5, p. 726-737. (with abstract).

Fessi et al., "Nanocapsule formation by interfacial polymer deposition following solvent displacement." International Journal of Pharmaceutics, 1989, vol. 55, No. 1, p. R1-R4.

Tsujimoto et al., "Evaluation of the permeability of hair growing ingredient encapsulated PLGA nanospheres to hair follicles and their hair growing effects." Bioorganic & Medicinal Chemistry Letters, 2007, vol. 17, p. 4771-4777.

Lademann et al., "Nanoparticles—An efficient carrier for drug delivery into the hair follicles." European Journal of Pharmaceutics and Biopharmaceutics, 2007, vol. 66, No. 2, p. 159-164.

Stout et al., "Finasteride Treatment of Hair Loss in Women." The Annals of Pharmacotherapy, 2010, vol. 44, No. 6, p. 1090-1097.

Friedman et al., "Allergic contact dermatitis to topical minoxidil solution: Etiology and treatment." Journal of the American Academy of Dermatology, 2002, vol. 46, No. 2, p. 309-312.

Matias et al., "Animal models of androgen-dependent disorders of the pilosebaceous apparatus. 1. The androchronogenetic alopecia (AGA) mouse as a model for male-pattern baldness." Archives of Dermatological Research, v. 281, p. 247-253, 1989.

Guterres et al. "Polymeric Nanoparticles, Nanospheres and Nanocapsules, for Cutaneous Applications" Drug Target Insights 2007:2 147-157.

Shim et al., "Transdermal delivery of mixnoxidil with block copolymer nanoparticles" Journal of Controlled Release 97 (2004) 477-484.

Venturini et al. "Formulation of lipid core nanocapsules" Colloids and Surfaces A: Physicochem. Eng. Aspects 375 (2011) 200-208.

FINASTERIDE AND MINOXIDIL POLYMERIC NANOPARTICLE ITS PROCESS OF PREPARATION, AQUEOUS SUSPENSION CONTAINING THE SAME, PHARMACEUTICAL COMPOSITION, AND ITS USE

This application is the United States national stage of International Application No. PCT/BR2013/000335, filed Aug. 30, 2013, which was published under PCT Article 21 in Portuguese as International Publication No. WO 2014/032152, and which claims benefit of Brazil Patent Application No. BR102012022036-9 filed Aug. 31, 2012 which is herein incorporated by reference.

FIELD OF THE INVENTION

The present invention relates to a pharmaceutical composition for topical application for the treatment of alopecia, said composition comprising polymeric nanoparticles, preferably nanocapsoids, as herein defined, containing two active ingredients, finasteride and minoxidil, and pharmaceutically acceptable additives and vehicles. The invention further includes a process for the preparation of polymeric nanoparticles, preferably nanocapsoids of finasteride and minoxidil, suitable for a topical application composition for the treatment of alopecia, as well as the use of said nanocapsoids for the preparation of a pharmaceutical composition.

FUNDAMENTS OF THE INVENTION

Hair loss, also called alopecia, can manifest itself in many forms. It can be irreversible in cases classified as scarring alopecia where there is the destruction of hair follicles; or reversible in non-scarred cases which have several causes and may originate from pharmacological treatments, diet, physiological or psychological stress, fungal infections, chemotherapy or genetic inheritance. Because of this, several pharmacological and non-pharmacological treatments (implants and laser applications) are being used in an attempt to reverse this situation.

In capillary therapy, in order for a drug to have the desired action, it is necessary for it to reach the hair follicle (in the epidermis), where the enzyme responsible for triggering the disease is located, without permeating the blood capillaries which supply the pilous follicle (avoiding a systemic action). Thus, for a formulation to be effective, it is necessary for it to be able to promote penetration and retention of the drug at its site of action (DRAKE, L. et al.; "The effects of finasteride on scalp skin and serum androgen levels in men with androgenetic alopecia." Journal of the American Academy of Dermatology, 1999, vol. 41, no. 4, p. 550-554). 30.

Androgenic alopecia is the transformation of mature hair follicles (terminal) to immature follicles (vellus) through successive capillary cycles with a shortening of the anagen phase time. Thus, due to the reduction in time of growth and development of the shaft, it becomes progressively shorter, thinner and often without color (INUI, S.; ITAMI, S.; "Molecular basis of androgenetic alopecia: From androgen to paracrine mediators through dermal papilla." Journal of Dermatological Science, 2011, vol. 61, p. 1-6). This is the most common type of alopecia and it affects mainly men, being related, among other factors, to the regulation of sex hormones. A greater understanding of androgenic baldness came from the studies of Hamilton (1942) who described the pattern of hair loss and the physiology as a process linked to a genetic predisposition of the hair follicle that occurs under the influence of androgens (Trueb, R M; "Molecular mechanisms of androgenetic alopecia." Experimental Gerontology, 2002 v. 37, no. 8-9, p. 981-990). However, there is no correlation between androgenic alopecia and testosterone, free testosterone and bioavailable testosterone levels. It is probable that the pathogenic bases of baldness are mediated through intracellular signaling in the hair follicle (INUI, S.; ITAMI, S.; "Molecular basis of androgenetic alopecia: From androgen to paracrine mediators through dermal papilla." Journal of Dermatological Science, 2011, vol. 61, p. 1-6).

Through the action of 5α-reductase enzyme, testosterone is converted to a more powerful hormone dihydrotestosterone (DHT). It is believed that its action is greater than that of testosterone for two main reasons: (i) DHT cannot be converted into estrogen by aromatases, maintaining only its purely androgenic activity, (ii) in vitro studies demonstrate that DHT binds with more affinity to the androgen receptor than testosterone (LIU, S.; YAMAUCHI, H.; "Different patterns of 5α-reductase expression, cellular distribution, and testosterone metabolism in human follicular dermal papilla cells." Biochemical and Biophysical Research Communications, 2008, 368 p. 858-864). The action of these androgen hormones occurs by their dissemination through the cell membrane with the purpose of binding to the intracellular androgen receptor. As a result of this binding, the hormone-receptor complex undergoes conformational changes, thus binding the complex with the promoter site in the DNA, triggering the production of messenger RNAs that will transcribe the genetic response (INUI, S.; ITAMI, S.; "Molecular basis of androgenetic alopecia: From androgen to paracrine mediators through dermal papilla." Journal of Dermatological Science, 2011, vol. 61, p. 1-6). With the binding of DHT to the androgen receptor present in the hair follicle, the response is the decrease in the anagen phase of the hair growth cycle, thus moving the hair to the early telogen phase (Ellis, J A; Harrap, S B; "The genetics of androgenetic alopecia." Clinics in Dermatology, 2001, vol. 19, p. 149-154).

Androgenic alopecia presents a pattern in hair loss, which facilitates the diagnosis and easily distinguishes it from other types. By default, initial loss of the hair shaft occurs on the frontal part or only on the vertex, and may expand to other regions. The degree of alopecia can be determined by the Norwood-Hamilton scale. This scale identifies three types of hair loss patterns: vertex pattern (where the loss of the shaft starts at the back), front pattern (where the loss of the shaft starts at the front) and the normal pattern (beginning with loss at both the front and the back), with all patterns being divided into seven stages of hair loss (Sinclair, R D; "Male androgenetic alopecia." The Journal of Men's Health & Gender, 2004 v. 1, no. 4, p. 319-327).

Currently, alopecia treatment can be both topical and systemic. Among the drugs approved by ANVISA (Brazil), the following can be cited: (i) as systemic, the medicine made of finasteride (1 mg) for oral use, marketed under the brand name Propecia®, which acts as a blocker of DHT hormone; and (ii) as topical: (a) a drug with a minoxidil base, marketed under the brand name Regain®/Rogain® mousse with 2% (for women) and 5% (for men) and (b) a drug based on alphaestradiol, marketed under the brand name Avicis® in the form of a 0.025% solution.

The active ingredients (finasteride and minoxidil) present several stability, bioavailability and formulation difficulties, that result from their physicochemical and biological/physiological properties. To solve or reduce the negative characteristics of the active ingredients, alternatives were researched to "protect them against degradation" or to "increase their solubility."

The development of new drug delivery systems has been the target of improvements directed towards the enhancement of their therapeutic efficacy and safety of use, by changing pharmacokinetic and pharmacodynamic aspects. Among the colloidal drug delivery systems, there are the polymeric nanoparticles and liposomes (Avnesh Kumari, Sudesh Kumar Yadav, Subhash C. Yadav, Biodegradable polymeric nanoparticle based drug delivery systems, Colloids and Surfaces B: Biointerfaces, Volume 75, Issue 1, Jan. 1, 2010, Pages 1-18; Vladimir P. Torchilin, RECENT ADVANCES WITH LIPOSOMES AS PHARMACEUTICAL CARRIERS, NATURE REVIEWS, VOLUME 4, FEBRUARY 2005, p 145). Because of their therapeutic potential and improved stability during storage and upon contact with biologic fluids, polymeric nanoparticles formed by biodegradable polymers have attracted an increased attention of researchers when compared to liposomes (SCHAFFAZICK, S H, et al.; "Characterization and physicochemical stability of nanoparticle polymeric systems for drug delivery." New Chemistry, 2003, Vol. 26, no. 5, p. 726-737).

Polymeric nanoparticles are colloidal drug carrier systems which have diameters between 10 and 1000 nm and are divided, according to their supramolecular architectures, into vesicles or matrices. Nanocapsules (vesicular) have an oily core surrounded by a polymer matrix, allowing the drug to be dispersed in the core and/or adsorbed in the polymeric wall. Nanospheres (matrices) do not have an oily core, only a polymeric structure, so the drug may be adsorbed or retained in the polymer matrix. Nanoparticles made of biodegradable polymers have been preferred since they have greater therapeutic potential, and high stability in biological fluids and during storage (SCHAFFAZICK, S H, et al.; "Characterization and physicochemical stability of nanoparticle polymeric systems for drug delivery." New Chemistry, 2003, Vol. 26, no. 5, p. 726-737).

Different physicochemical processes may be employed for the preparation of these nanoparticle systems, such as: (i) interfacial deposition of preformed polymers, (b) salting-out, and (c) emulsification-diffusion. Among the main techniques for nanocapsule preparation, the interfacial deposition of preformed polymers proposed by Fessi et al in 1989 should be highlighted (FESSI, H.; et al; "Nanocapsule formation by interfacial polymer deposition following solvent displacement." International Journal of Pharmaceutics, 1989, vol. 55, no. 1, p. R1-R4), wherein the polymer is dissolved in the organic solvent together with the oily component, the lipophilic surfactant and the drug or active ingredient to be encapsulated. This organic/oily phase is injected under moderate agitation, over an aqueous phase, which is composed of water and a hydrophilic surfactant. This mixture spontaneously yields nanocapsules with average diameters between 200 and 500 nm. Finally, the organic solvent and excess water are removed.

Most topical products available for the treatment of alopecia are formulated with the active ingredients dissolved in a water-alcohol solution. However, due to the low permeability of some drugs through the keratin layer, only a fraction of the applied dose reaches the site of action, penetrating the pores and hair follicles (TSUJIMOTO, H. et al.; "Evaluation of the permeability of hair growing ingredient encapsulated PLGA nanospheres to hair follicles and their hair growing effects." Bioorganic & Medicinal Chemistry Letters, 2007, vol. 17, p. 4771-4777). As a result, hair growth using these products does not exceed consumer expectations, leading to lack of adherence to treatment. Recent studies have confirmed the hypothesis that nanoparticles can penetrate effectively in the pilous follicles (Lademann, J., et al.; "Nanoparticles—An efficient carrier for drug delivery into the hair follicles." European Journal of Pharmaceutics and Biopharmaceutics, 2007, vol. 66, no. 2, p. 159-164) reaching deep functional structures wherein they remain stored for a few days. In the case of non-particulate substances, such long term effects have not been observed in pilous follicles or in the stratum corneum. In principle, the stratum corneum lacks the reservoir characteristic for topically applied substances since these substances remain localized on the surface of the skin or in the upper cell layers (which are continuously removed by peeling). Therefore, pilous follicles become, in long term, the only reservoirs for non-particulate substances of topical use. These observations show that pilous follicles are important targets for drug delivery, since they are surrounded by a dense network of blood capillaries and dendritic cells (Langerhans cells).

For example, the effect of nanospheres of poly(lactide-co-glycolide) (PLGA) containing three different active ingredients (Hinokitiol, glycyrrhetinic acid and 6-benzylaminopurine) for hair growth was assessed in vivo (TSUJIMOTO, H., et al.; "Evaluation of the permeability of hair growing ingredient encapsulated PLGA nanospheres to hair follicles and their hair growing effects." Bioorganic & Medicinal Chemistry Letters, 2007, vol. 17, p. 4771-4777). Analyzing the fluorescence intensity of these active ingredients in human scalp biopsies, the authors found that the nanospheres had a permeability effect in the pores 2 to 2.5 times higher when compared to the control group of the same active ingredients in a buffer solution (PBS). It was also possible to see an increase in the capillary activity, whose cycle is passed from the rest phase to the growth phase, suggesting that PLGA nanospheres may be promising carriers for drugs in hair follicles.

To date, there are few papers in the literature that report the carrying of finasteride in nanoparticle systems. Document US20060204588, owned by Elan Pharma International Limited, discloses a pharmaceutical composition containing nanoparticulate finasteride (having average size less than 2000 nm) and at least one surface stabilizer which may be adsorbed by or associated with the surface of the active ingredient. As to the method of preparation of the nanoparticulate finasteride formulation, this method consists in dispersing finasteride in a liquid dispersion medium, and mechanically reducing its particle size.

Patent application US20110117045, owned by Fujifilm Corporation, is a product based on protein nanoparticles containing an active ingredient for hair treatment; the product consists of nanoparticles produced from protein (such as casein, collagen, gelatin, albumin, among others) which also contains an active ingredient that promotes hair growth, and includes finasteride and minoxidil as one of these active ingredients.

Document WO2005000258, owned by Amorepacific Corportation, describes self-assembled polymeric nanoparticles comprising an amphiphilic polymer and a physiologically active ingredient; wherein the amphiphilic polymer comprises polycaprolactone and polyethylene glycol as a hydrophobic and hydrophilic block, and the physiologically active ingredient is comprised by said amphiphilic polymer. The physiologically active ingredient can be finasteride (as specified in claim 10; see also examples 45-47) or minoxidil (see page 8, lines 8-18). The motivation of the claimed improvements, i.e., the use of an amphiphilic polymer in the formation of nanoparticles containing an active ingredient, is to reduce the colloidal instability which causes the precipitation or flocculation that occurs when a hydrophobic polymer is used in the preparation of nanoparticles.

However, it is desirable to use a homopolymer which is technically less complex and simpler to obtain than a copolymer which is actually a structure in polymer blocks, wherein the ratio of the hydrophilic and lipophilic portions is difficult to control, thus causing problems in the subsequent formation of nanoparticles, especially nanocapsules.

Furthermore, the use of block copolymers which are prepared in a 1:1 ratio of the hydrophilic and lipophilic portions causes a lack of flexibility in the hydrophile-lipophile balance (HLB) which can limit the quality of nanotechnological formulation. The possibility of varying the concentration of stabilizer (hydrophilic emulsifier or surfactant) is an advantage in preparing nanoparticles. Lipophilic homopolymers can be formulated as nanoparticles by employing stabilizers in varying proportions in the formulation, allowing an optimization of physical stability of the nanotechnology colloids.

SUMMARY OF THE INVENTION

The present invention aims to provide an effective pharmaceutical composition for topical treatment of alopecia, said composition comprising polymeric nanoparticles, preferably nanocapsoids containing finasteride and minoxidil, a pharmaceutically acceptable vehicle; and optionally additives. The invention also includes the preparation of polymeric nanoparticles, preferably finasteride and minoxidil nanocapsoids, which are comprised by said pharmaceutical composition.

A first embodiment of the invention relates to a topical pharmaceutical composition comprising a therapeutically effective amount of polymeric nanoparticles, preferably nanocapsoids, containing finasteride and minoxidil, stably dispersed in a pharmaceutically acceptable vehicle; and optionally containing additives.

In a second embodiment, said polymeric nanoparticles, preferably nanocapsoids are formed by preparing the organic and aqueous phases, wherein:
  (i) The organic phase comprises: (a) a hydrophobic polymer, (b) a fixed oil, (c) at least one low HLB lipophilic surfactant, (d) a solvent, (e) a co-solvent and (f) finasteride; and
  (ii) The aqueous phase comprises: g at least one hydrophilic surfactant, h minoxidil and i water.

In a third embodiment, the invention comprises the use of polymeric nanoparticles, preferably nanocapsoids, for the preparation of a pharmaceutical composition for the treatment of alopecia.

The process for preparing the composition of the invention comprises two stages. The first stage concerns the preparation of polymeric nanoparticles, preferably the nanocapsoids of the invention, comprises the steps of: (i) preparing the organic phase by dissolving the hydrophobic polymer and finasteride, a fixed oil, at least one low HLB surfactant, in an organic solvent and a co-solvent; (ii) preparing the aqueous phase by dissolving minoxidil, at least one hydrophilic surfactant, preferably neutral, in water; (iii) injecting the organic phase in the aqueous phase to allow formation of the primary emulsion of nanoparticles on the interface of the two phases, the mixture being maintained under stirring for a time sufficient for adequate encapsulation of the active ingredients; (iv) removing at least one organic solvent and recovering the aqueous phase containing the nanocapsules.

After preparation of the nanoparticles, they are suspended in a suitable vehicle, optionally containing additives such as dispersants, moisturizers, emollients agents, thickeners, sequestering, preservatives, antioxidants, fragrances and the like.

DETAILED DESCRIPTION OF THE INVENTION

Figure 1:
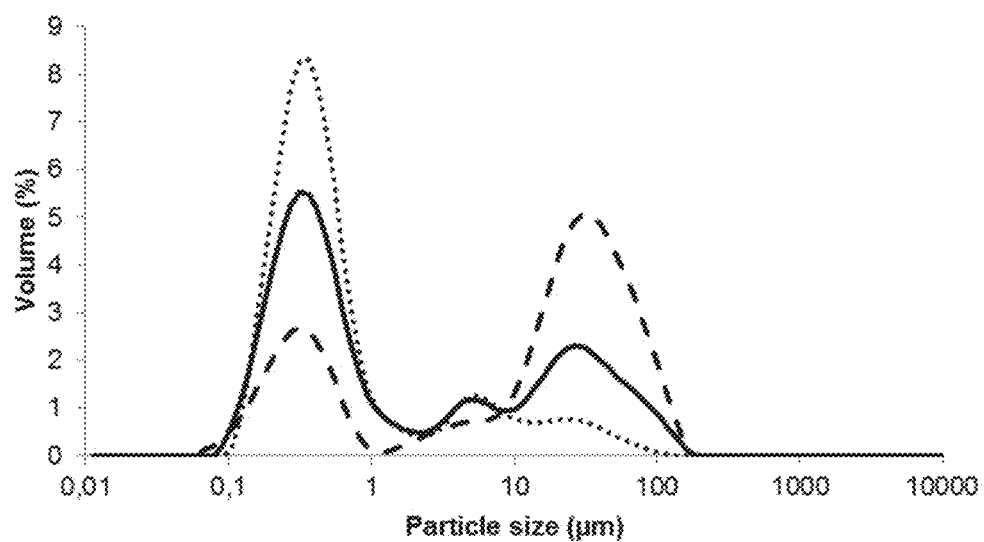
FIG. 1 shows a comparison of the physical profile of the finasteride nanocapsoids 0.20% and minoxidil 0.20% (n=3) [FIG. 1] and nanocapsoids of finasteride 0.25% (n=3) [Graphic 2].
Figure 1:
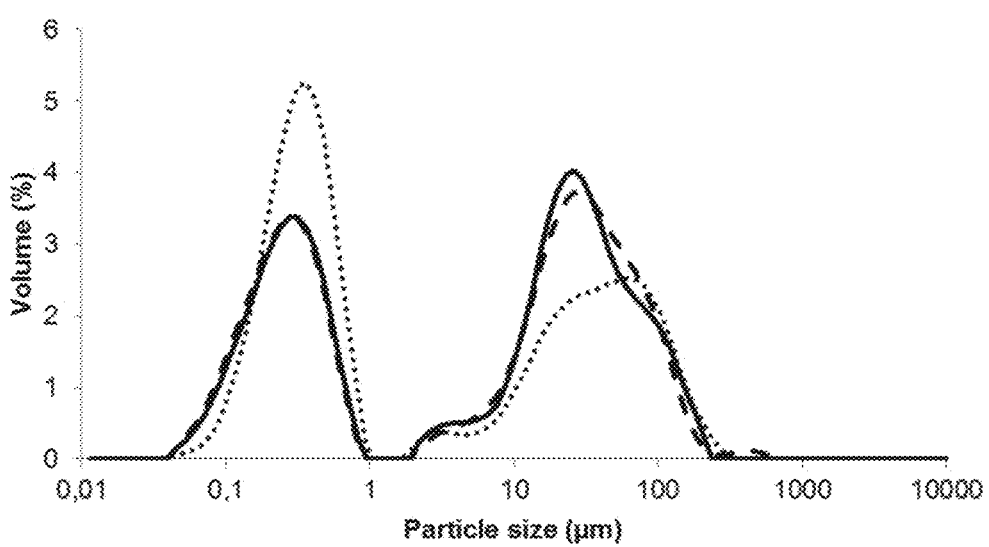

The present invention relates to a pharmaceutical composition effective for the topical treatment of alopecia, said composition comprising nanoparticulate systems, preferably containing the nanocapsoids of finasteride and minoxidil, a pharmaceutically acceptable vehicle; and optionally containing additives.

The term nanocapsoid, as used herein, means polymeric nanocapsules prepared by a nanoencapsulation process in which, in the organic phase, a solvent and a co-solvent are employed.

The invention also includes a process for the preparation of polymeric nanoparticles, preferably nanocapsoids comprising finasteride and minoxidil, which are comprised by said composition.

Finasteride is a synthetic azosteroid with potent selective antagonist action on 5α-reductase type 2 enzymes. Finasteride acts by irreversibly binding to the enzyme, preventing the conversion of testosterone to its active metabolite, dihydrotestosterone (DHT). The use of finasteride was initially approved for the reduction of prostate size associated with urinary obstruction (benign prostatic hyperplasia), since DHT in men, although responsible for prostate development, can be involved in development of hyperplasia. However, it has been observed that patients taking this drug also presented a reversal in alopecia symptoms. For this reason, the development of studies to investigate the potential of finasteride in the treatment of baldness had begun (Sinclair, R D, "Male androgenetic alopecia: Part II." The Journal of Men's Health & Gender, 2005, vol. 2, no. 1, p. 38-44). A study by Kaufmann et al (2008) with 1553 men aged 18 to 41 years evaluated the action of finasteride in doses of 1 mg daily against placebo for five years. The result of treatment with finasteride led to a decrease in the probability of visible hair loss, compared to the increased likelihood of visible hair loss in patients treated with placebo. In this study, at the end of the five years, 75% of placebo-treated patients developed baldness and only 10% of patients treated with finasteride developed the disease. A review of the safety and efficacy of finasteride use for treating androgenic alopecia in women showed in conclusion that this drug can be used safely and effectively in cases wherein topical treatment with minoxidil is not effective (Stout, S M; STUMPF, J L; "Finasteride Treatment of Hair Loss in Women." The Annals of Pharmacotherapy, 2010, vol. 44, no. 6, p. 1090-1097).

Minoxidil was introduced as the therapy in the treatment of hypertension in 1965; however, it was observed that orally administered minoxidil caused hypertrichosis. Resulting from the evidence from this and subsequent studies, minoxidil was approved by the Food and Drug Administration (FDA) for treatment of androgenic alopecia in males (at a concentration of 5%) and women (at a concentration of 2%). However, although the topical solution of minoxidil presents proven safety and effectiveness, adverse effects may occur with its use. Friedman and colleagues (2002) reported cases of contact allergy, which included pruritus, erythema and dryness of the scalp. Some patients showed sensitivity to minoxidil, but mainly to the propylene glycol component present in the topical solution as a co-solvent and absorption enhancer (Friedman, E S, et al; "Allergic contact dermatitis to topical minoxidil solution: Etiology and treatment." Journal of the American Academy of Dermatology, 2002, vol. 46, no. 2, p. 309-312).

The present invention avoids the disadvantages and adverse effects associated with the systemic administration of finasteride and topical minoxidil and proposes a topical application composition of finasteride and minoxidil for the treatment of alopecia with reduced side effects caused by these two active ingredients.

The invention is based on the preparation of polymeric nanoparticles, preferably nanocapsoids, of finasteride and minoxidil, by means of an interfacial deposition of preformed polymer, wherein it is firstly made the dissolution of finasteride, of a hydrophobic polymer, of a fixed oil and at least one low HLB surfactant (Hydrophilic Lipophilic Balance) in an organic solvent and a co-solvent, to form the organic phase; and dissolution of minoxidil, and at least one hydrophilic surfactant, preferably neutral, in water, to form the aqueous phase.

Although nanoparticles, a term which includes nanospheres, nanocapsules and nanocapsoids, can be advantageously produced by the present invention, the invention is, preferably, particularly directed to the preparation of nanocapsoids, preferably carried out by the interfacial deposition method. However, it should be clear that other methods can be used to produce the nanocapsules of the invention.

Said polymeric nanoparticles, preferably nanocapsoids are formed from the organic and aqueous phases, as follows:
(i) The organic phase comprises: (a) a hydrophobic polymer, (b) a fixed oil, (c) at least one low HLB lipophilic surfactant, (d) a solvent, (e) a co-solvent and (f) finasteride; and
(ii) The aqueous phase comprises: (g) at least one hydrophilic surfactant, (h) minoxidil and (i) water.

Said polymer used to encapsulate finasteride is a hydrophobic polymer selected from the group consisting of vinyl polymers, polyesters, polyamides, polyurethanes and polycarbonates. Preferably, the hydrophobic polymer used is a biodegradable polymer from the group of polyesters having a melting point of less than 120° C. More preferably, the biodegradable hydrophobic polymer is from the group of polyesters, is a poly(lactide); a poly (glycolide); copolymers of poly(lactide-co-glycolide); a polycaprolactone; a copolymer of polycaprolactone with polyester, with polyamide, with polyurethane or with a vinyl polymer; and most preferably, it is the poly($\epsilon$-caprolactone).

Said fixed oil used in the organic phase of the preparation of polymeric nanoparticles of the invention is selected from the group consisting of canola oil, soybean oil, olive oil and medium-chain triglycerides; with medium-chain triglycerides being preferably used. Among the medium-chain triglycerides selected from the group of triglycerides of capric and caprylic acid, propylene glycol dicaprylocaprate, macrogolglycerides of oleyl, laureola and linoleoyl. Still more preferably, the use as a fixed oil, of medium-chain triglycerides, are the triglycerides of capric and caprylic acid.

The lipophilic surfactant used in said organic phase of preparation of polymeric nanoparticles of the invention is a surfactant of low HLB, preferably having a value in the range of 3 to 6, being solid or liquid, preferably solid, selected from the group consisting of sorbitan monostearate, sorbitan distearate, sorbitan tristearate, caprylocaproyl macrogolglycerides, propylene glycol laurates, propylene glycol caprylate, glyceryl monostearate, polyglyceryl oleate, or mixtures thereof. Preferably, the lipophilic surfactant used in the organic phase of the invention is sorbitan monostearate.

The solvent used in the organic phase of preparation of the polymeric nanoparticles of the present invention is an organic solvent selected from the group consisting of acetone, dimethylsulfoxide, dimethylformamide, N-methylpyrrolidone, dioxane, acetonitrile, methyl ethyl ketone, or other solvent which presents physicochemical properties of intermolecular interaction with water. In a preferred embodiment of the invention, the organic solvent is preferably acetone.

Said co-solvent used in the organic phase of preparation of the polymeric nanoparticles, preferentially nanocapsoids, of the present invention is selected from the group consisting of methanol, ethanol, propanol, and isopropanol or other alcohol, mono-, di-, tri- or polyhydroxylated, glycerol, sorbitol, polyethylene glycol, mannitol or propylene glycol. In a preferred embodiment of the invention, the co-solvent is preferably ethanol. The use of ethanol in the organic phase as a co-solvent promotes the formation of nanocapsoids with unexpexted nanotechnological quality, since the polymer poly ($\epsilon$-caprolactone) is insoluble in methanol or ethanol. However, to have nanoscopic granulometry, the components of the organic phase should be water soluble and employed below the saturation concentration.

The aqueous phase contains at least one hydrophilic surfactant for the preparation of the nanoparticles, preferentially nanocapsoids, of the invention, preferably being an emulsifier such as polyoxygenated polymers, or ionic surfactants such as lecithin or a neutral surfactant selected from the group consisting of polysorbate 20, polysorbate 60 or polysorbate 80, macrogol stearate, macrogol cetostearyl ether, macrogol lauryl ether, macrogol oleyl ether, macrogol oleate, polyoxyl castor oil, hydrogenated polyoxyl castor oil, or mixtures thereof. Preferably, polysorbate is employed, and more preferably, polysorbate 80, for the aqueous phase of the preparation of the nanoparticles of the invention.

The aqueous suspension of polymeric nanoparticles comprises:
The organic phase (a) from 0.01% to 30.0% (w/w) of a hydrophobic polymer, (b) from 0.01% to 50.0% (w/w) of a fixed oil (c) from 0.01% to 50.0% (w/w) of at least one lipophilic surfactant of low HLB, preferably solid (d) from 10% to 80% (w/w) of organic solvent, (e)

0.001% to 50% (w/w) of a co-solvent; and (f) from 0.001% to 80.0% (w/w) of finasteride; and The aqueous phase (g) from 0.001% to 80.0% (w/w) of minoxidil, (h) from 0.05% to 20.0% (w/w) of at least one hydrophilic surfactant, (i) 10% to 90% (w/w) water.

In a preferred formulation of the aqueous suspension, the polymeric nanoparticles, preferably nanocapsoids, comprise:

in the organic phase (a) from 0.05% to 20.0% (w/w) of a hydrophobic polymer, preferably poly (caprolactoneϵ); (b) from 0.05% to 20.0% (w/w) of a fixed oil, preferably medium-chain triglycerides; (c) from 0.05% to 20.0% (w/w) of at least one lipophilic surfactant, preferably sorbitan monostearate; (d) from 10% to 80% (w/w) of an organic solvent, preferably acetone; (e) 0.001% to 50% (w/w) of a co-solvent, preferably ethanol; and (f) from 0.005% to 50.0% of finasteride; and in the aqueous phase (g) from 0.005% to 50.0% (w/w) minoxidil; (h) from 0.05% to 20.0% (w/w) of at least one hydrophilic surfactant, preferably polysorbate; and (i) from 10% to 90% (w/w) water.

The pharmaceutical composition for the treatment of alopecia contains: (A) nanocapsoids of the present invention, comprising (a) from 0.01% to 2.5% (w/w) of finasteride; (b) from 0.01% to 10.0% (w/w) minoxidil; (c) from 0.1% to 10.0% (w/w) of a hydrophobic polymer, preferably poly (ϵ-caprolactone ϵ); (d) from 0.1% to 5.0% (w/w) of a fixed oil, preferably medium-chain triglycerides; (e) 0.1% to 5.0% (w/w) of at least one low HLB lipophilic surfactant, preferably sorbitan monostearate; (f) from 0.001% to 10% (w/w) of a hydrophilic surfactant, preferably polysorbate 80; and (B) a pharmaceutically acceptable carrier, wherein the amounts of the nanocapsoid components are a percentage of the final formulation and said nanocapsoids are dispersed in said pharmaceutically acceptable vehicle.

A preferred pharmaceutical composition for treating alopecia of the present invention comprises from 0.01 to 1.0% (w/w) of finasteride and 0.01 to 2.0% (w/w) of minoxidil in the form of polymeric nanoparticles, preferably in the form of nanocapsoids, dispersed in a pharmaceutically acceptable vehicle.

The pharmaceutical composition for the treatment of alopecia of the present invention is intended for topical administration and is in the form of a solution, gel or lotion.

The pharmaceutical composition for the treatment of alopecia optionally contains additives such as dispersants, surfactants, moisturizing agents, emollients agents, thickeners, sequestering agents, preservatives, antioxidants, fragrances and the like.

The following are specific embodiments of the invention. However, it should be understood that such examples are provided for illustrative purposes only, and that various modifications or changes, in light of the herein disclosed embodiments, will be suggestive to specialists in the art and must be included within the spirit and scope of this disclosure and the scope of the accompanying claims.

EXAMPLE 1

Preparation of Nanocapsoids of the Invention Containing Finasteride 0.20% and Minoxidil 0.20%

EXAMPLE 1.1

Preparation of Finasteride and Minoxidil Nanocapsoids

The suspensions of nanocapsoids of finasteride were prepared from an organic solution of a mixture of acetone and ethanol containing poly (ϵ-caprolactone), medium chain triglycerides (triglycerides of capric and caprylic acids), sorbitan monostearate and finasteride employing the composition described in Table 1.

TABLE 1

Composition of the suspensions of poly (ϵ-caprolactone) nanocapsoids containing finasteride 0.20% and minoxidil 0.20% based on the final formulation

|  | Quantity |
|---|---|
| Organic Phase |  |
| Triglycerides of capric and caprylic acids | 3.30 ml |
| Sorbitan monostearate | 770 mg |
| Poly(-caprolactone) | 1000 mg |
| Acetone | 200 ml |
| Ethanol | 50 ml |
| Finasteride | 200 mg |
| Aqueos Phase |  |
| Polisorbate 80 | 770 mg |
| Minoxidil | 200 mg |
| Distilled Water | 500 ml |

The polymer (poly (ϵ-caprolactone)) was solubilized in the organic phase along with finasteride, triglycerides of caprylic and capric acid, and the low HLB surfactant (sorbitan monostearate) under moderate heating between 20° C. and 40° C. preferably at 40° C., employing acetone as the solvent and ethanol as the co-solvent. The neutral surfactant (polysorbate), and minoxidil were dissolved in water to form the aqueous phase. After solubilization of all components of the organic and aqueous phases, the organic phase was injected, using a funnel, on the aqueous phase.

After the formation of the primary emulsion of nanocapsoids of the invention, it was maintained under moderate agitation for 10 minutes, and then concentrated to a final volume of 100 ml in a rotary evaporator under reduced pressure in a thermostatic bath in the evaporation flask between 10° C. and 80° C., preferably between 30° C. and 45° C. to eliminate the organic solvent and co-solvent and excess water, to adjust the final concentration of finasteride and minoxidil.

EXAMPLE 1.2

Characterization of the Formulation

A. Determination of pH

Determination of pH was performed in a potentiometer calibrated with a buffer of pH 4.0 and 7.0, directly in the suspensions, by the average of three repetitions.

B. Determination of the Particle Diameter and Polydispersion Index by Multiple Light Scattering.

For the determination of the diameter and polydispersity index of nanoparticle suspension by dynamic light scattering, the Zetasizer® nano-device model ZEN 3600 ZS, Malvern, USA was used. For both, the samples were diluted in MilliQ® water (filtered through a 0.45 micron filter, Millipore Millex-HP) 500 times at room temperature and the results were determined by the average of three repetitions.

C. Determination of Particle Size Distribution by Laser Diffractometry

To assess whether there is a concomitant presence of micrometer population, analyses of particle size were performed by laser diffraction (Mastersizer 2000, Malvern, UK). Analyses were carried out by adding a sample of the formulation in the accessory dispersion containing about 100 ml of distilled water. The amount added to that was enough to achieve obscuration between 0.02 and 0.10. To prevent interference of the background signal (from the water) it was measured before addition of the sample.

D. Zeta Potential

The zeta potential of the nanoparticle suspension was determined by electrophoresis methodology with the Zetasizer® nano-ZS model ZEN 3600 device (Malvern, USA). The determination was carried out using 500 times dilution in 10 mM NaCl solution (filtered through a 0.45 micron filter, Millipore Millex-HP), and results obtained were the average of three determinations.

E. Viscosity

The viscosity of the suspensions was measured using a vibrational viscometer (SV-10, A & D Company, Japan). To achieve this, the viscosity was measured directly in the suspensions for 30 seconds with data collection every 5 seconds at a temperature of 25±1.0° C.

F. Assay of Finasteride in the Formulation

For the assay of finasteride, the suspension of polymeric nanoparticles was treated with acetonitrile in ultrasson (for 30 min) resulting in the extraction of the drug from the formulation. The drug assay was then performed by high performance liquid chromatography (HPLC).

The analysis was performed on the Perkin Elmer chromatograph Series 200, using ultraviolet-visible detector (with $\lambda$=210 nm for the finasteride), LiChrospher 100 RP-18 column (5 μm, 250×4 mm) pre-column of the same material (5 um) and isocratic mobile phase of acetonitrile: water (75:25), flow of 1 mL min −1, injection volume of 100 μL.

G. Assay of Minoxidil in the Formulation

The assay of minoxidil was carried out in a spectrophotometer. For both, the polymeric nanoparticle suspension was treated with methanol in ultrasson (for 30 minutes) resulting in the extraction of the pharmacological formulation. Shortly after this, the samples were read in a spectrophotometer, at a wavelength of 248 nm, using a formulation of white nanocapsoides as a reference beam (prepared in the same manner without the presence of drugs).

H. Checking for the Presence of Crystals

To verify any simultaneous presence of crystals (drug dispersed in the aqueous phase) quantification by HPLC of a freshly prepared formulation of the drug was initially performed. After this formulation was divided into two samples: the first was allowed to be still and the second was stirred before the assay, which was performed again after 30 days. From the sample which was kept still, only one aliquot of the supernatant (preventing any movement) was collected. From the other, an aliquot (corresponding to 20% of the supernatant) was collected after vortexing for 15 seconds.

I. In Vivo Assay for Determining the Ability of Hair Recovery

The technique used was a modification of the technique described by Matias et al (1989), approved by the Ethics Committee of the Federal University of Rio Grande do Sul.

For the experiments, B6CBAF1 hybrid female mice were used from the vivarium of the University of Vale do Itajaí (UNIVALI). The animals were under standard conditions of temperature and relative humidity during the experiment, with light and dark cycles of 12 hours each. All animals received a subcutaneous injection of 1% testosterone dispersed in a mixture of polysorbate 80 in water (100 mg·mL$^{-1}$) at a dose of 1 mg per day. There were five injections per week for 4 weeks.

In the first week the animals received only injections of testosterone. On the first day of the second week of the experiment, all animals had the hair removed from their backs with Veet® depilatory cream, for the total removal of hair. After removal of hair, daily injections of testosterone were maintained, and a daily topical application of the formulation was added to the treatment, depending on the treatment group (placebo, treatment, control). For the treatment groups, the optimized formulation containing the nanocapsoids of the present invention was used, which was compared with the results of the formulation of finasteride 0.25% disclosed in the co-pending patent application of the same Applicant of the present patent application. The formulation for topical treatment of androgenic alopecia, commercially available under the brand name Pilexil® (Serenoa serrulata extract 22.0%, Valeant) was also tested.

To monitor the growth of hair, photographs were taken on days 1, 15, and 23. On the 24th day the animals were sacrificed by cervical dislocation. A sample of skin from the backs of 4 animals of each group was removed and evaluated microscopically. To this end, the slides were sent to the Zanol laboratory, which were prepared and stained with hematoxylin-eosin. Then we proceeded to the analysis with a light microscope (Zeiss—Primo Star coupled to the camera Canon Power Shot, PC1250) to determine which growth stage the hair was in. (MATIAS, J R, et al.; "Animal models of androgen-dependent disorders of the pilosebaceous apparatus. 1. The androchronogenetic alopecia (AGA) mouse as a model for male-pattern baldness. Archives of Dermatological Research, v. 281, p. 247-253, 1989).

To quantify the data obtained by histology, it was proceeded the counting of mature follicles (with pigmentation and inserted in the adipose tissue) of each of the histological slides from each group. Thus, we analyzed 4 slides per group, and the count was based on 3 different foci of the same slide, totaling 12 fields analyzed per group. For a comparison between the groups, statistical analysis by ANOVA ($\alpha$=0.05) was made.

J. In Vivo Assay for Determining the Ability of Hair Recovery

The analyses were performed with a transmission electron microscope (JEOL, JEM 1200 Exll, Electron Microscopy Center—UFRGS) operating at 80 kV. The diluted suspensions were deposited on the carbon support film in grids, negatively stained with uranyl acetate solution (2% w/v) and observed using a magnitude of 250,000 times.

EXAMPLE 1.3

Physicochemical Characterization of the Nanocapsoid Formulation Containing Finasteride 0.20% and Minoxidil 0.20%

Table 2 shows the diameter values (for multiple light scattering), polydispersion index, zeta potential, pH and viscosity for the nanocapsoids formulation of the invention containing the combination of finasteride and minoxidil.

TABLE 2

Physicochemical characterization of the nanocapsoids formulation containing the combination of finasteride and minoxidil (finasteride 0.20% and minoxidil 0.20%) of the invention, compared with the characterization of the formulation of finasteride 0.25% (as disclosed in application co-pending from the same Applicant of the present application)

| Analysis | Formulation 0.20% finasteride and 0.20% minoxidil | Formulation 0.25% finasteride |
|---|---|---|
| Average diameter (nm) | 255 ± 2 | 221 ± 3 |
| Polydispersion index | 0.22 ± 0.02 | 0.14 ± 0.03 |
| Zeta potencial (mV) | −11.7 ± 1.2 | −14.9 ± 2.7 |
| pH | 6.4 ± 0.1 | 4.6 ± 0.1 |
| Viscosity (mPa · s) | 1.25 ± 0.19 | 1.21 ± 0.07 |

This formulation containing the two active ingredients, finasteride and minoxidil, presented physicochemical characteristics close to those of the formulation containing only finasteride (nanocapsules of poly (caprolactone) containing 0.25% of the active ingredient), as, for example, the diameter and the zeta potential. However, the pH was shown to be closer to the neutral value, probably due to the presence of the minoxidil solution in the external aqueous phase.

FIG. 1 shows a comparison between the granulometry-profile of the nanocapsoids of finasteride and minoxidil (finasteride 0.20% and minoxidil 0.20%) of the invention and of the nanocapsules of finasteride (finasteride 0.25%). As noted, the nanocapsoids of the invention containing the combination have a slightly decreased micrometer population compared to the nanometer. To facilitate this view, the profiles of the triplicate of each formulation lot were presented separately in FIG. 1.

Figure 2:
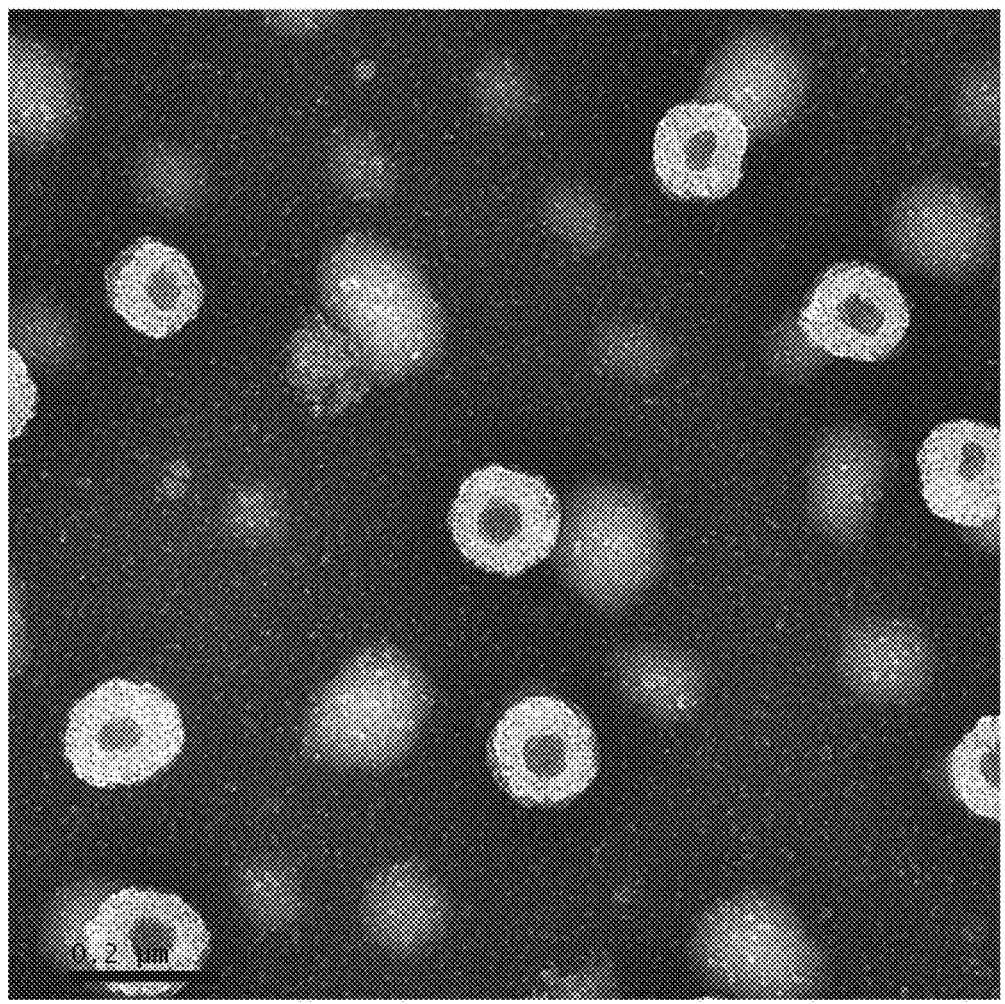
FIG. 2 shows a transmission electron microscopy of the 0.1% finasteride nanocapsoids.

For a better evaluation of the morphological characteristics of the formulation, analysis of transmission with electron microscopy as shown in FIG. 2 was performed.

EXAMPLE 1.4

Assay for Determining the Capillary Recovery Capacity of the Nanocapsoids of Finasteride and Minoxidil of the Invention The improvement in efficiency of the capillary recovery capacity by use of the nanocapsoid formulation containing the combination of the drugs finasteride and minoxidil of the invention, was assessed with an in vivo assay with this formulation, and was compared to the results using the nanocapsule formulation containing 0.25% finasteride and the use of a formulation available in the market having antiandrogen action indicated for the treatment of alopecia: Pilexil® (Valeant), with the active ingredient Serenoa serrulata extract.

Figure 3:
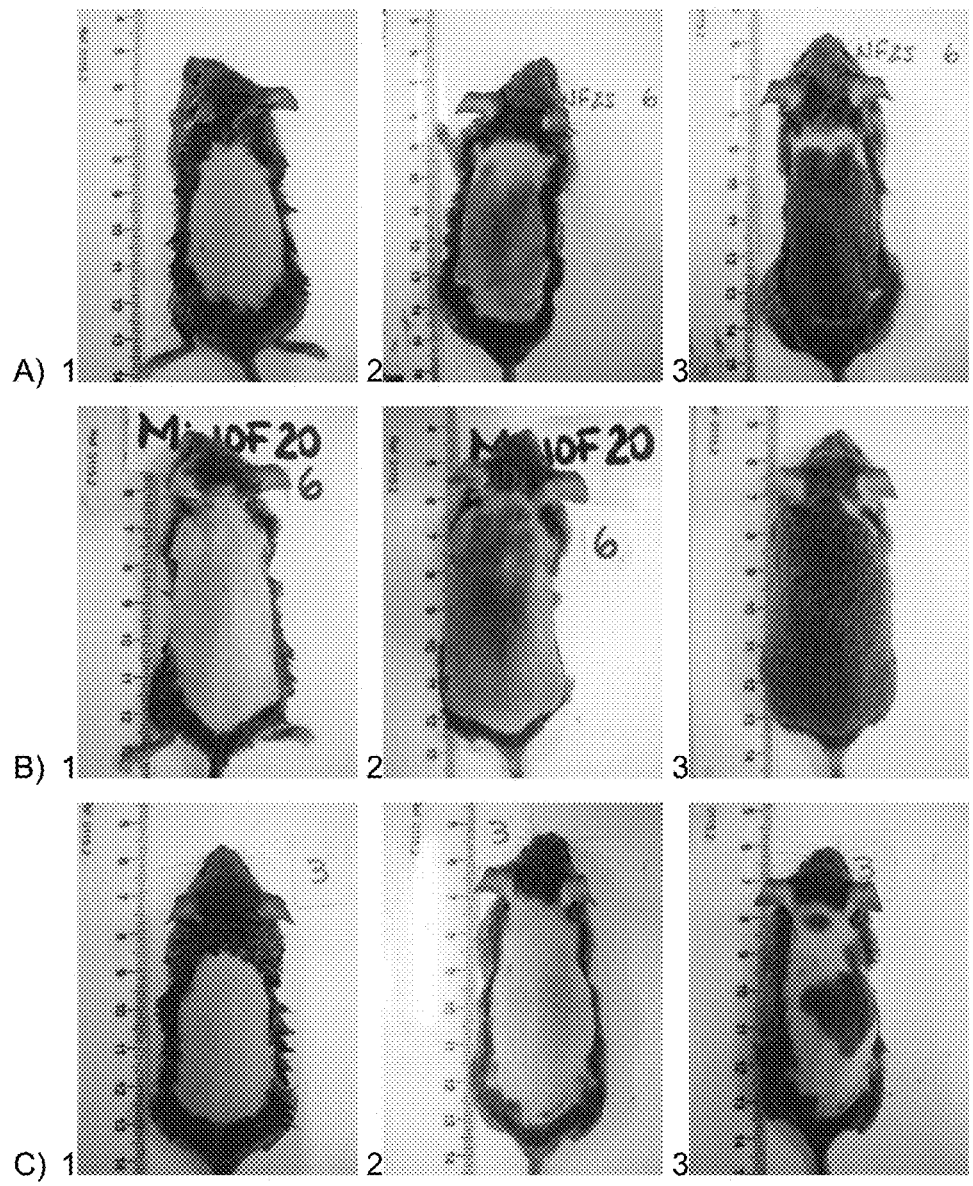
FIG. 3 shows photographs of the animals on day 1 (photo 1), day 15 (photo 2) and day 23 (photo 3) of treatment for the groups treated with: (A) nanocapsules of finasteride 0.25% (B) nanocapsoids of finasteride 0.20%, minoxidil 0.20% and (C) Pilexil®.

To perform the test, animals of the B6CBAF1 lineage were treated for a week with subcutaneous injections of testosterone, and in the second week, had the back depilated for treatment and determination, thus, the capillary recovery capacity of the tested formulations. FIG. 3 shows the comparison of treatments through the pictures of the representative animals from each group on days 1, 15 and 23; treated with (A) the nanocapsule formulation containing 0.25% finasteride, as disclosed in the co-pending application of the same Applicant of the present application; (B) the formulation of the invention containing nanocapsoids comprising finasteride 0.20% and minoxidil 0.20%; and (C) Pilexil®.

As noted, the formulation of the present invention presented a visual result well superior to the product in the market for the treatment of androgenetic alopecia (Pilexil®).

When compared with the formulation of nanocapsules containing finasteride 0.25%, the result was slightly higher. This result can be best observed when all the animals of the groups were analyzed together. One can observe a more complete covering of hair on all the animals treated with the formulation of the present invention. In turn, in the group treated with the formulation of nanocapsules containing 0.25% finasteride, some animals still showed some areas without full coverage by the new coat of hair.

Figure 4:
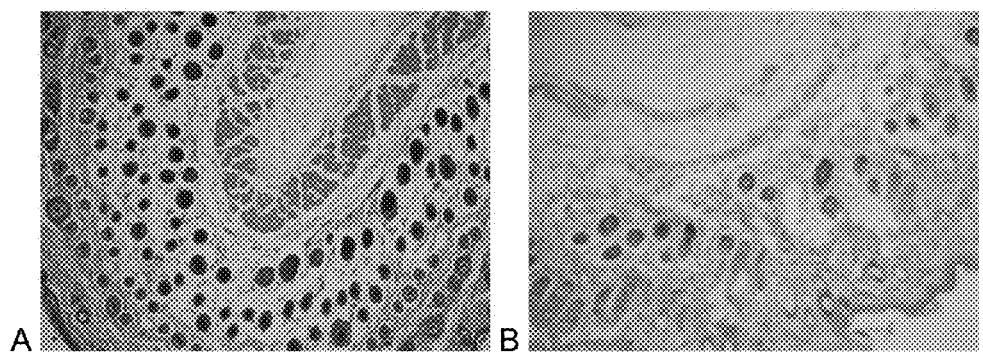
FIG. 4 illustrates the histopathological analysis of the skin removed from the back of the animals after 23 days of treatment with (A) nanocapsoids of finasteride 0.20%, minoxidil 0.20% and (B) Pilexil®.
Figure 5:
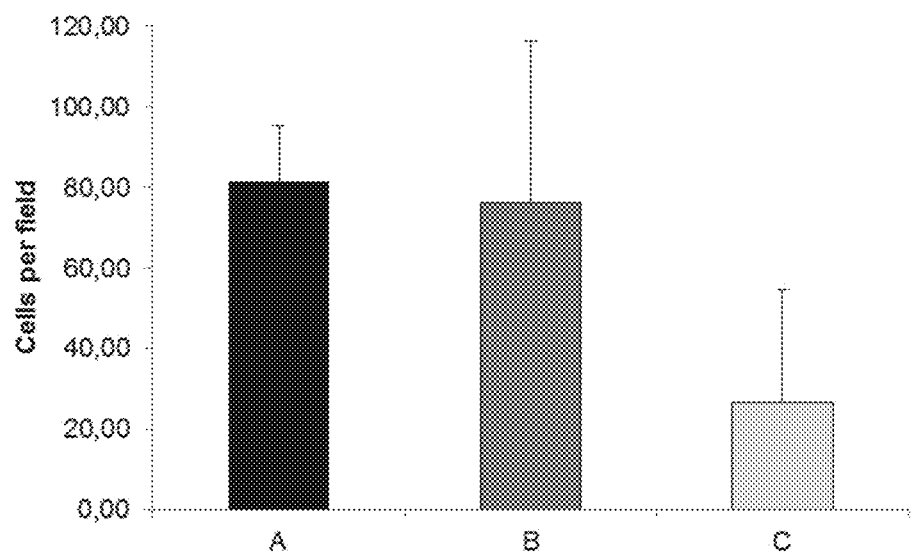
FIG. 5 shows the mean number of mature follicles analyzed by histological specimen (n=12) animals treated with: (A) nanocapsules of finasteride 0.25%, (B) nanocapsoids of finasteride 0.20%, minoxidil 0.20% and (C) Pilexil®.

The histopathological analysis, shown in FIG. 4, and cell counts, shown in FIG. 5, from the slide images showed significant differences between the groups (ANOVA, $\alpha=0.05$).

The nanocapsoid formulation with a combination of the drugs finasteride and minoxidil of the present invention exhibited a number of follicles per field significantly higher than that of the Pilexil® formulation, being similar to that shown by the formulation of nanocapsules containing 0.25% finasteride (ANOVA, $\alpha=0.05$).

Although the visual results, through the accompanying photographs, of hair growth using the nanocapsoids formulation containing minoxidil and finasteride of the present invention have been slightly higher compared to those presented by the use of the nanocapsule formulation containing 0.25% finasteride, the results of the cell counts showed similarity between these two formulations. Thus, it can be concluded that the addition of minoxidil assists in accelerating the growth of the hair (revival) without favoring however the development (maturation) thereof. That is, minoxidil accelerates the growth of hair, but does not reverse the capillary involution that occurring in androgenic alopecia; this reversal is provided by finasteride.

EXAMPLE 2

Pharmaceutical Compositions Comprising Minoxidil and Finasteride Nanocapsoids

EXAMPLE 2.A

Formulation in the Form of Topical Solution

Nanocapsoids of finasteride and minoxidil are prepared as described in Example 1.1. The topical solution is prepared resulting in the formulation in Table 3.

TABLE 3

Formulation in form of a topical solution containing the nanocapsoids suspension containing 0.025% finasteride and 0.20% minoxidil.

| Components | Percentage |
| --- | --- |
| Triglycerides of capric and caprylic acids | 3.23 |
| Sorbitan monostearate | 0.77 |
| Poly(-caprolactone) | 1.00 |
| Finasteride | 0.025 |
| Polisorbate 80 | 0.77 |
| Minoxidil | 0.20 |
| Distilled water | 94.005 |

EXAMPLE 2.B

Formulation in the Form of Topical Gel

Nanocapsoids of finasteride and minoxidil are prepared as described in Example 1.1.

The nanocapsoid suspensions, prepared as described in Example 2.A, were thickened with 0.2% Carbopol® 940. Triethanolamine qs was added to obtain a suitable viscosity for topical application. The resulting gel has the formulation shown in Table 4.

TABLE 4

Formulation in form of a topical gel containing the nanocapsoid suspension of 0.05% finasteride and 0.25% minoxidil.

| Components | Percentage |
| --- | --- |
| Triglycerides of capric and caprylic acids | 3.23 |
| Sorbitan monostearate | 0.77 |
| Poly(-caprolactone) | 1.00 |
| Finasteride | 0.05 |

TABLE 4-continued

Formulation in form of a topical gel containing the nanocapsoid suspension of 0.05% finasteride and 0.25% minoxidil.

| Components | Percentage |
| --- | --- |
| Polisorbate 80 | 0.77 |
| Carbopol 940 | 0.20 |
| Distilled water | 93.73 |
| Triethanolamine | qs |

EXAMPLE 2.C

Formulation in Form of a Topical Lotion

Initially, phase 1 is prepared as described in Example 2.A, and the composition was employed from phase 1 in Table 5. Separately, the components were merged from phase 2 in a water bath at 50° C. and removed from heating after fusion. Next, add phase 3 to phase 1 and disperse under constant magnetic stirring. Add this mixture of phases 1 and 3 in the molten phase 2 and cool to 40° C. under moderate mechanical agitation to avoid air incorporation.

TABLE 5

Formulation in form of a topical lotion containing the nanocapsoid suspension containing 0.1% finasteride and 0.3% minoxidil.

| | Percentage (%) |
| --- | --- |
| Components Phase 1 | |
| Triglycerides of capric and caprylic acids | 3.23 |
| Sorbitan monostearate | 0.77 |
| Poly(-caprolactone) | 1.00 |
| Finasteride | 0.10 |
| Polisorbate 80 | 0.77 |
| Minoxidil | 0.30 |
| Distilled water | 89.53 |
| Components Phase 2 | |
| Coconut oil | 2.0 |
| Propylparaben | 0.2 |
| Methylparaben | 0.1 |
| Components Phase 3 | |
| Salcare SC91 (INCI: Polyacrylamide and C13-14 Isoparaffin and Laureth-7) | 2.0 |

All publications and patent applications mentioned in this specification are indicative of the level of those skilled in the art to which the invention relates. All publications and patent applications are incorporated herein by reference to the same extent as if each individual publication or patent application were each specifically and individually indicated to be incorporated for ease of reference.

Although certain embodiments have been described, they are presented in an exemplary mode only, and are not intended to limit the scope of the invention. In fact, the new embodiments described herein may be implemented in a variety of other forms; more than that, various omissions, substitutions and changes in the form of the embodiments described herein may be made without diverging from the spirit of the invention. The claims and their equivalents accompanying this description are considered to cover such forms or modifications as they may be within the scope and spirit of the invention.

The invention claimed is:

1. A polymeric nanoparticle comprising the active ingredients finasteride and minoxidil, wherein said polymeric nanoparticle is in the form of a nanocapsoid formed from:
    (i) an organic phase comprising:
        (a) a hydrophobic polymer that is a biodegradable polymer from a group of polyesters having a melting point of less than 120° C.,
        (b) a fixed oil,
        (c) a lipophilic surfactant having low hydrophilic-lipophilic balance (HLB),
        (d) an organic solvent,
        (e) a co-solvent, and
        (f) finasteride; and
    (ii) an aqueous phase comprising:
        (g) a hydrophilic surfactant,
        (h) minoxidil, and
        (i) water.

2. The polymeric nanoparticle according to claim 1, wherein said biodegradable polymer from the group of polyesters having a melting point of less than 120° C. is selected from the group consisting of a poly(lactide); poly (glycolide); copolymers of poly(lactide-co-glycolide); poly-caprolactone; and a copolymer of polycaprolactone with a polyester, with a polyamide, with a polyurethane or with a vinyl polymer.

3. The polymeric nanoparticle according to claim 2, wherein said polycaprolactone is a poly (ϵ-caprolactone).

4. The polymeric nanoparticle according to claim 1, wherein said fixed oil is a medium-chain triglyceride.

5. The polymeric nanoparticle according to claim 4, wherein said medium-chain triglyceride is selected from the group consisting of capric and caprylic acids triglycerides, propylene glycol di(caprylate/caprate), and oleyl macrogol-glycerides.

6. The polymeric nanoparticle according to claim 1, wherein said lipophilic surfactant of low HLB with a value in the range of 3 to 6 is selected from the group consisting of sorbitan monostearate, sorbitan distearate, sorbitan tristearate, capril caprylic macrogolglycerides, propylene glycol laurates, propylene glycol caprylates, glyceryl monostearate, and polyglyceryl oleates.

7. The polymeric nanoparticle according to claim 6, wherein said lipophilic surfactant of low HLB is sorbitan monostearate.

8. The polymeric nanoparticle according to claim 1, wherein said organic solvent is acetone.

9. The polymeric nanoparticle according to claim 1, wherein said co-solvent is ethanol.

10. The polymeric nanoparticle according to claim 1, wherein said hydrophilic surfactant is a neutral hydrophilic surfactant selected from the group consisting of polysorbate 20, polysorbate 60, polysorbate 80, macrogol stearate, macrogol cetostearyl ether, macrogol lauryl ether, macrogol oleyl ether, macrogol oleate, polyoxyl castor oil, hydrogenated polyoxyl castor oil, and mixtures thereof.

11. The polymeric nanoparticle according to claim 10, wherein said neutral hydrophilic surfactant is polysorbate 80.

12. The polymeric nanoparticles according to claim 1, wherein:
    (i) the organic phase comprises:
        (a) from 0.05% to 20.0% (w/w) of a poly (ϵ-caprolactone),
        (b) from 0.05% to 20.0% (w/w) of medium-chain triglycerides, (c) from 0.05% to 20.0% (w/w) of sorbitan monostearate,
(d) from 10% to 80% (w/w) of acetone,
(e) from 0.001% to 50% (w/w) of ethanol, and
f) from 0.005% to 50.0% (w/w) of finasteride; and
(ii) the aqueous phase comprises:
(g) from 0.05% to 20.0% (w/w) of polysorbate 80,
(h) from 0.005% to 50.0% (w/w) of minoxidil, and
(i) from 10% to 90% (w/w) of water.

13. A pharmaceutical composition for the treatment of alopecia comprising:
(A) the polymeric nanoparticle according to claim 1, and
(B) a pharmaceutically acceptable carrier;
wherein the polymeric nanoparticles are dispersed in said pharmaceutically acceptable carrier.

14. The pharmaceutical composition according to claim 13, comprising 0.01 to 1.0% (w/w) of finasteride and 0.01 to 2.0% (w/w) of minoxidil.

15. The pharmaceutical composition according to claim 13, wherein the pharmaceutical composition is in the form of a solution, gel or lotion for topical administration.

16. The pharmaceutical composition according to claim 13, wherein it further comprises additives selected from dispersants, surfactants, moisturizing agents, emollients, thickeners, sequestering agents, preservatives, antioxidants, and fragrances.

* * * * *